United States Patent
Kabakov et al.

(10) Patent No.: US 9,597,055 B2
(45) Date of Patent: Mar. 21, 2017

(54) FETAL SCALP DOPPLER DEVICE AND SYSTEM

(75) Inventors: Serguei Kabakov, Savage, MD (US); Steven M. Falk, Baltimore, MD (US); Karsten A. Russell-wood, Baltimore, MD (US)

(73) Assignee: General Electric Company, Schenectady, NY (US)

( * ) Notice: Subject to any disclaimer, the term of this patent is extended or adjusted under 35 U.S.C. 154(b) by 1259 days.

(21) Appl. No.: 12/986,765

(22) Filed: Jan. 7, 2011

(65) Prior Publication Data

US 2012/0179045 A1 Jul. 12, 2012

(51) Int. Cl.
*A61B 8/02* (2006.01)
*A61B 8/08* (2006.01)
(Continued)

(52) U.S. Cl.
CPC ........ *A61B 8/0866* (2013.01); *A61B 5/02411* (2013.01); *A61B 8/02* (2013.01);
(Continued)

(58) Field of Classification Search
None
See application file for complete search history.

(56) References Cited

U.S. PATENT DOCUMENTS

RE28,990 E    10/1976  Hon et al.
4,942,882 A *  7/1990  Bellinson ...................... 600/588
(Continued)

FOREIGN PATENT DOCUMENTS

JP    1107745 A    4/1989
WO    00/30534 A1  6/2000
(Continued)

OTHER PUBLICATIONS

Search Report from corresponding GB Application No. 1200130.1 May 4, 2012.
(Continued)

*Primary Examiner* — Joseph M Santos Rodriguez
(74) *Attorney, Agent, or Firm* — Andrus Intellectual Property Law, LLP

(57) ABSTRACT

A fetal pulse monitor includes an ultrasound crystal. An ultrasound controller is electrically connected to the ultrasound crystal and operates the ultrasound crystal to produce ultrasound signals and receive reflected ultrasound signals. A wireless transmitter is electrically connected to the ultrasound controller. A biocompatible housing at least partially surrounds the ultrasound crystal, ultrasound controller, and the wireless transmitter. A system for monitoring fetal heart rate includes a fetal pulse monitor configured for insertion into a womb of a patient and for attachment to a fetus within the womb. The fetal pulse monitor includes an ultrasound crystal, an ultrasound controller electrically connected to the ultrasound crystal, and a wireless transmitter electrically connected to the ultrasound controller. A patient monitoring device is external to the womb and includes a wireless receiver and a processor that detects instantaneous fetal heart rate from the received ultrasound signal. A graphical display is communicatively connected to the patient monitoring device. The graphical display is operated by the patient monitoring device to present the determined fetal heart rate.

18 Claims, 4 Drawing Sheets

(51) Int. Cl.
    *A61B 5/024*     (2006.01)
    *A61B 8/12*     (2006.01)
    *A61B 8/00*     (2006.01)
    *A61B 5/00*     (2006.01)

(52) U.S. Cl.
    CPC .............. *A61B 8/12* (2013.01); *A61B 8/4236* (2013.01); *A61B 8/488* (2013.01); *A61B 5/6814* (2013.01)

(56) References Cited

U.S. PATENT DOCUMENTS

| | | | |
|---|---|---|---|
| 4,966,152 A | 10/1990 | Gang et al. | |
| 5,257,627 A | 11/1993 | Rapoport | |
| 5,265,613 A | 11/1993 | Feldman et al. | |
| 5,394,877 A * | 3/1995 | Orr et al. | 600/459 |
| 5,474,065 A | 12/1995 | Meathrel et al. | |
| 5,538,005 A | 7/1996 | Harrison et al. | |
| 5,882,300 A * | 3/1999 | Malinouskas et al. | 600/300 |
| 6,093,151 A | 7/2000 | Shine et al. | |
| 6,151,520 A | 11/2000 | Combs | |
| 6,171,263 B1 | 1/2001 | Sullivan | |
| 6,200,279 B1 * | 3/2001 | Paltieli | 600/588 |
| 6,292,679 B1 | 9/2001 | Sheard | |
| 6,340,346 B1 * | 1/2002 | Almog et al. | 600/300 |
| 6,379,305 B1 | 4/2002 | Eugley | |
| 6,416,471 B1 | 7/2002 | Kumar et al. | |
| 6,816,744 B2 * | 11/2004 | Garfield et al. | 600/546 |
| 6,843,771 B2 | 1/2005 | Lo et al. | |
| 6,863,653 B1 | 3/2005 | Zanelli et al. | |
| 7,336,985 B2 | 2/2008 | Wallace et al. | |
| 7,758,522 B2 | 7/2010 | Pandit | |
| 2004/0236193 A1 * | 11/2004 | Sharf | 600/302 |
| 2008/0312537 A1 * | 12/2008 | Hyuga | 600/459 |

FOREIGN PATENT DOCUMENTS

| | | | |
|---|---|---|---|
| WO | 01/13796 A1 | 3/2001 | |
| WO | 0178577 | 10/2001 | |
| WO | 02096288 | 12/2002 | |
| WO | 02098271 A2 | 12/2002 | |
| WO | 2005025419 A1 | 3/2005 | |
| WO | 2005110236 A1 | 11/2005 | |
| WO | WO 2008146202 A1 * | 12/2008 | A61B 8/00 |
| WO | 2009013701 A2 | 1/2009 | |

OTHER PUBLICATIONS

Breeveld-Dwarkasing, et al; Cervical Dilatation Related to Uterine Electromyographic Activity and Endocrinological Changes During Prostaglandin F2α-Induced Parturition in Cows; Biology of Reproduction, vol. 68, (2003), pp. 536-542.

van Engelen, E. et al; EMG activity of the muscular and stromal layer of the cervix in relation to EMG activity of the myometrium and cervical dilatation of PGF2α induced parturition in the cow; Theriogenology, vol. 67, (2007), pp. 1158-1167.

Corometrics® 170 Series; Operator's Manual; Manual P/N 2002023-001 Rev.D; GE Medical Systems Information Technologies.

Search Report and Written Opinion from NL Application No. 2008075 dated Nov. 14, 2012.

* cited by examiner

FETAL SCALP DOPPLER DEVICE AND SYSTEM

BACKGROUND

The present disclosure is related to the field of fetal monitoring. More specifically, the present disclosure is related to monitoring the fetal heart rate.

Fetal heart rate (FHR) is a diagnostic tool used by clinicians during pre-delivery and labor to monitor the health and condition of the unborn fetus.

Typically, FHR during labor and delivery is measured as a biopotential using a subcutaneous electrode attached to the fetus after the rupture of the fetal membrane or amnion.

The transdermal electrode is usually detached from the fetus during the course of delivery, which results in interruption in the obtaining of this biopotential.

BRIEF DISCLOSURE

A fetal scalp doppler includes an ultrasound crystal. An ultrasound controller is electrically connected to the ultrasound crystal. The ultrasound controller operates the ultrasound crystal to produce ultrasound signals and to receive reflected ultrasound signals. The ultrasound controller receives the reflected ultrasound signals from the ultrasound crystal. A wireless transmitter is electrically connected to the ultrasound controller. The wireless transmitter transmits the ultrasound signal to a remote device for signal processing. A biocompatible housing at least partially surrounds the ultrasound crystal, ultrasound controller and the wireless transmitter. The biocompatible housing is configured for insertion into a womb for monitoring a fetus within the womb.

An alternative embodiment of a fetal scalp doppler includes a fetal heart rate monitor configured for insertion into a womb of a patient and for attachment to a fetus within the womb. The fetal scalp doppler includes an ultrasound crystal. The fetal scalp doppler further includes an ultrasound controller that is electrically connected to the ultrasound crystal. The ultrasound controller operates the ultrasound crystal to produce ultrasound signals and receive reflected ultrasound signals. The ultrasound controller receives the reflected ultrasound signals from the ultrasound crystal. The fetal scalp doppler further includes a wireless transmitter electrically connected to the ultrasound controller The wireless transmitter transmits the ultrasound signal. A patient monitoring device is external to the womb. The patient monitoring device includes a wireless receiver that receives the ultrasound signal from the wireless transmitter of the fetal heart rate monitor. The patient monitoring device further includes a processor that detects the instantaneous fetal heart rate from the received ultrasound signal. A graphical display is communicatively connected to the patient monitoring device. The graphical display is operated by the patient monitoring device to present the determined fetal heart rate.

A fetal scalp doppler for monitoring the heart rate of a fetus internal to the mother's womb includes at least one ultrasound crystal that produces an ultrasound beam. An acoustic lens is secured relative to the at least one ultrasound crystal such that the acoustic lens shapes the ultrasound beam produced by the at least one ultrasound crystal. An ultrasound controller is communicatively connected to the at least one ultrasound crystal. The ultrasound controller operates the at least one ultrasound crystal to produce the ultrasound beam and receives a returned ultrasound signal from the at least one ultrasound crystal. A wireless transmitter is communicatively connected to the ultrasound controller. The wireless transmitter receives the returned ultrasound signal from the ultrasound controller and broadcasts the returned ultrasound signal. A biocompatible housing is disposed at least partially around the at least one ultrasound crystal, acoustic lens, ultrasound controller, and wireless transmitter.

DETAILED DESCRIPTION

Figure 1:
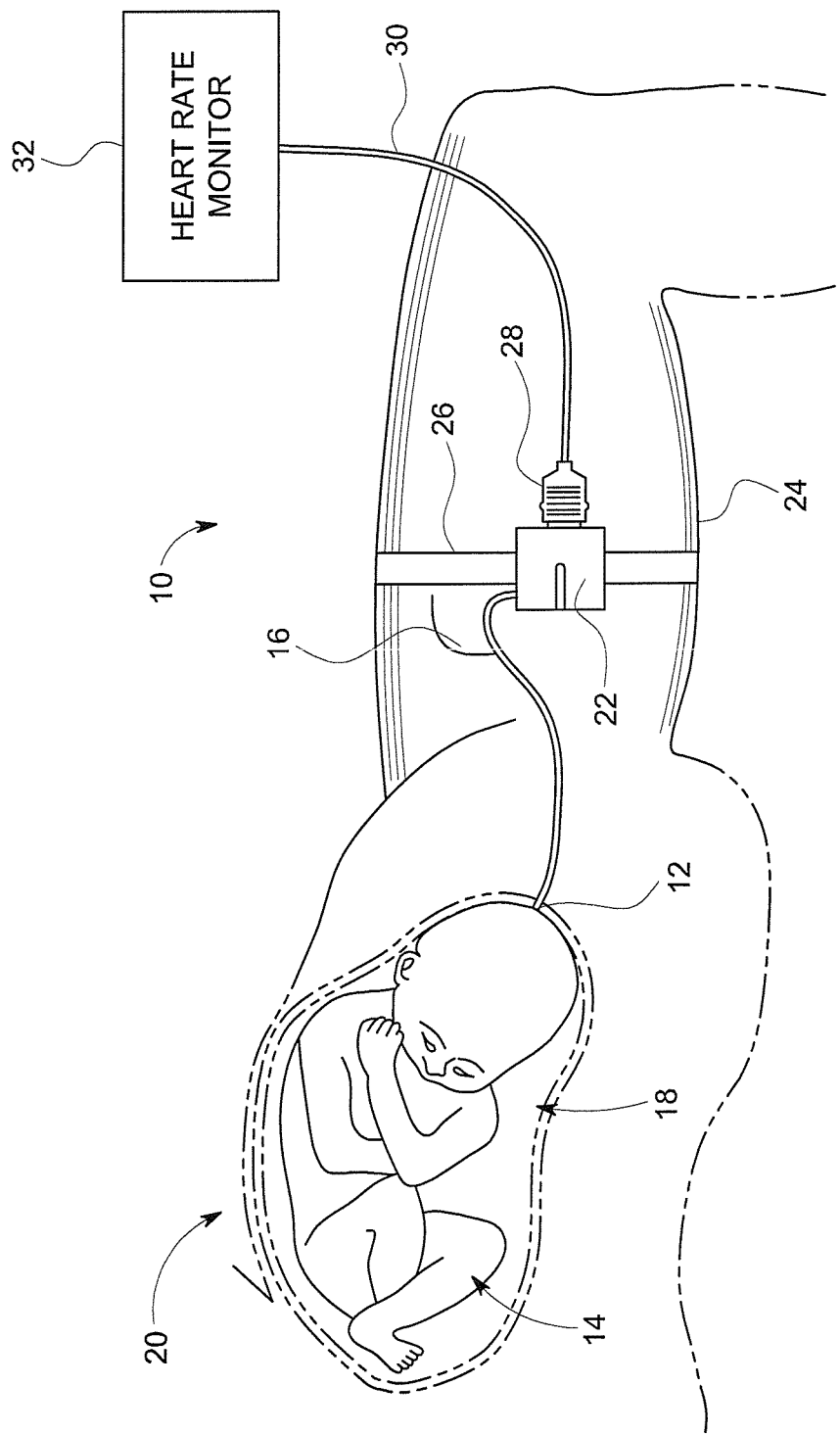
FIG. 1 depicts a prior art fetal heart rate monitor.

FIG. 1 depicts a known biopotential based fetal heart rate monitoring system 10. The fetal heart rate monitoring system 10 includes a subcutaneous electrode 12, such as a corkscrew electrode, that is attached to the fetus 14 by securing the electrode 12 under the scalp of the fetus 14. A lead wire 16 extends out of the womb 18 of the mother 20.

The electrocardiographic (ECG) signals obtained from the fetus 14 are differential potentials and therefore a ground or other comparative potential is required. This is obtained with an electrode patch 22 that is secured to a leg 24 of the mother 20. In one embodiment, the electrode patch 22 is secured to the mother's leg 24 through the use of an elastomeric band 26. The electrode patch 22 further directs both the biopotential received from the fetus 14 and the biopotential received from the mother's leg 24 through a connector 28 and a data cable 30 to a heart rate monitor 32. It is understood that in embodiments, the data cable 30 is a wireless communication connection (not depicted).

The heart rate monitor 32 processes the received biopotentials to derive the ECG of the fetus 14. Various physiological parameters can be derived from the fetal ECG, including FHR. The FHR monitoring system 10 has proven effective in monitoring fetal heart rate inutero; however, during the course of delivery, the acquisition of the biopotentials from the fetus 14 is interrupted due to a loss of one or more of the signals. This signal loss can occur from detachment of the sub-dermal electrode 12 from the fetus 14, the electrode patch 22 from the mother 20, or disconnection of either the lead wire 16 or the data cable 30. Additionally, if during delivery it is determined that the fetus 14 is to be delivered by Caesarian section, the fetus 14 must be disconnected from the heart rate monitor 32.

In either event, once the baby has been delivered, the baby is no longer connected to the heart rate monitor 32 and the diagnostic information provided by the baby's ECG is not available to a clinician in evaluating the condition of the newborn baby.

Figure 2:
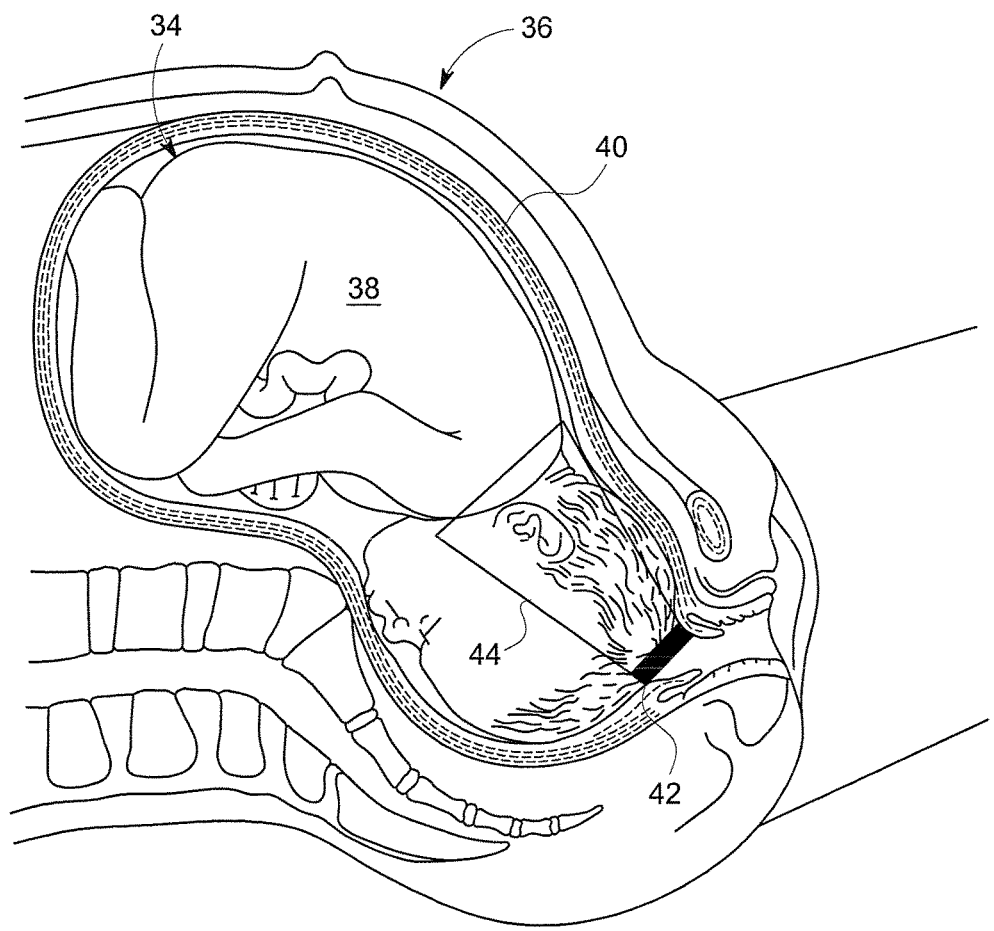
FIG. 2 depicts the intrauterine placement of an embodiment of fetal scalp doppler.

FIG. 2 is a cross sectional view of a womb 34 of a mother 36 within which a fetus 38 is disposed. The mother 36 is typically in labor and is about to deliver the fetus 38. The fetal membrane, or amnion 40, has been ruptured in order to gain access to the fetus 38. A fetal scalp doppler 42, as disclosed in further detail herein, is secured to the head of the fetus 38. The fetal scalp doppler 42 projects an ultrasonic beam 44 through at least a portion of the fetus 38 and wirelessly broadcasts the returned ultrasound signals as will be disclosed in further detail herein.

Pulse rate can serve as an alternative to heart rate, particularly if the pulse rate is obtained from one or more major systemic vessels. Fetal pulse rate is able to be determined from the ultrasonic signals returned to the fetal scalp doppler 42 when the fetal scalp doppler 42 is connected to the scalp of a fetus 38. The returned signals are representative of the blood flows in at least one of the carotid artery and jugular vein. When the returned ultrasonic signal includes signals from the blood flows in at least one of the carotid artery and jugular vein, the pulse in one or both of these vessels are repeatably trackable. The blood flow towards the fetal scalp doppler 42 in the carotid artery creates a positive doppler shift in the returned ultrasonic signal and the blood in the jugular vein away from the fetal scalp doppler 42 creates a negative doppler shift in the returned ultrasonic signal. Returned pulses with these shifts repeat at the fetal pulse rate. If the ultrasonic beam 44 includes both the carotid artery and the jugular vein, then the returned ultrasonic signal will include a segment exhibiting both the positive doppler shift and the negative doppler shirt in short succession. This combined segment can also be tracked to determine fetal pulse rate.

Figure 3:
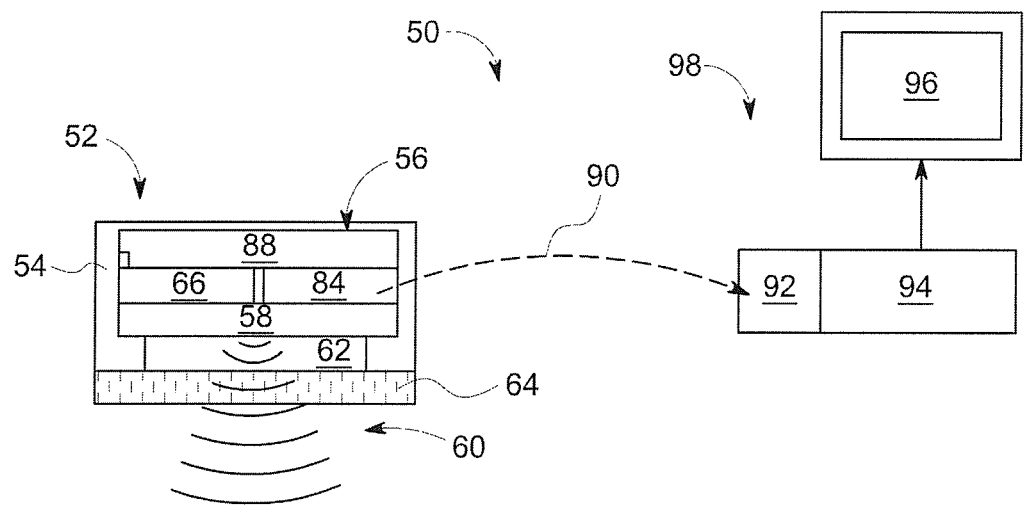
FIG. 3 is a schematic diagram of an embodiment of a fetal scalp doppler.

FIG. 3 is a schematic diagram of fetal scalp doppler 50. The fetal scalp doppler 50 includes front end 52. The front end 52 of the fetal scalp doppler 50 includes a biocompatible housing 54 within which at least a portion of the electronic components of the front end 52 are disposed. The housing 54 is both constructed from a material and in a manner such that the front end 52 may be inserted into the womb of the mother and secured to the fetus without the risk of damage to the electronics within the front end 52 as disclosed herein, or cause harm to the mother or fetus, such as from electrical shock.

The front end 52 includes electronics 56 that are at least partially disposed within the housing 54.

Figure 4:
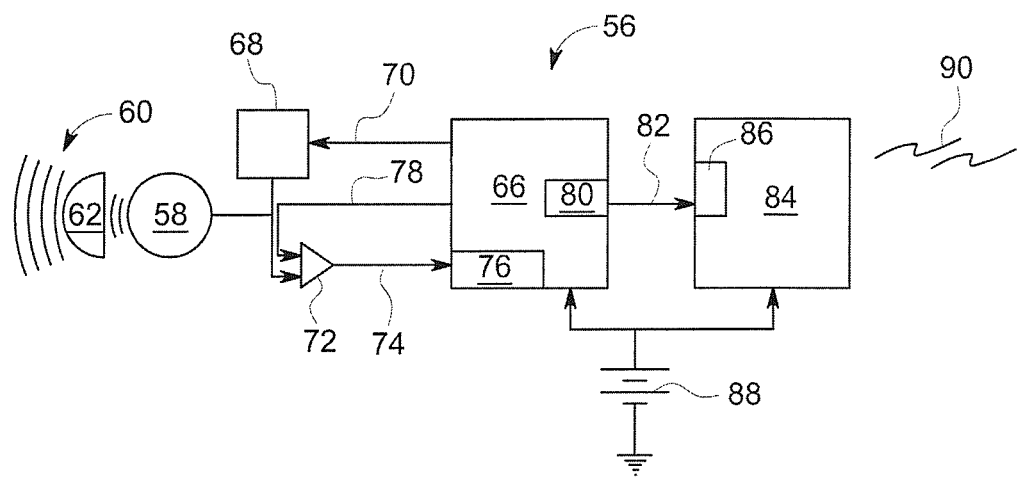
FIG. 4 is a further schematic diagram of an embodiment of a fetal scalp doppler front end.

FIG. 4 depicts an alternative schematic diagram of an embodiment of the electronics 56 shown in schematic form. Unless specifically noted, the disclosure herein refers to both FIGS. 3 and 4 wherein like reference numerals are used to reference like structures. The electronics 56 include an ultrasound crystal 58. In one embodiment, the ultrasound crystal 58 is a piezoelectric ultrasound crystal. In a further embodiment, the ultrasound crystal 58 is a plurality of ultrasound crystals that are operated as an ultrasound crystal array (not depicted).

The ultrasound crystal 58 produces an ultrasonic beam 60 as shown in FIG. 3. The ultrasonic beam 60 reflects off of objects or physiological structures and the reflected ultrasound signals are returned to the ultrasound crystal 58. The front end 52 includes an acoustic lens 62. The acoustic lens 62 performs the function of shaping ultrasound beam 60 from the ultrasound crystal 58 in order to direct the ultrasonic beam 60 in a general manner as depicted in FIG. 2. More specifically, the acoustic lens 62 spreads the ultrasonic beam 60 so that the ultrasonic beam 60 encompasses at least one of the carotid artery and jugular vein of the fetus. An embodiment of the acoustic lens 62 shapes the ultrasound beam 60 and directs the beam 60 in a manner such as to cover both the carotid artery and the jugular vein.

The inclusion of the acoustic lens 62 to spread the ultrasonic beam 60 beyond the shape of the ultrasonic beam as normally produced by the ultrasound crystal 58 provides an advantage to a clinician in that the fetal scalp doppler front end 52 need not be secured to the head of the fetus at a precise location and the pulse in at least one of the carotid artery and particular vein can still be detected. After the rupture of amnion, the exact positioning and orientation of the head of the fetus is sometimes unknown. Furthermore, the clinician can have difficulty in identifying an exact placement to align the fetal scalp doppler with the jugular vein or carotid artery. Therefore, by spreading the ultrasonic beam 60 with the acoustic lens 62, the range of positions and orientations of the fetal scalp doppler on the head of the fetus are greatly increased which promote ease of clinician use.

An adhesive layer 64 is disposed at one end of the front end 52. In one embodiment, the adhesive layer 64 serves as both an adhesive compound that secures the end 52 to the head of the fetus and also, the adhesive layer 64 is a substance selected for its ultrasonic coupling properties and therefore enhances the quality of the returned ultrasound signal received by the ultrasound crystal 58. In an alternative embodiment, the adhesive layer 64 is a removable patch that is kept separate from the front end 52 prior to use of the front end 52. Just before the front end 52 is secured to the head of the fetus, the adhesive layer 64 is applied to the front end 52. In such an embodiment wherein the front end 52 is a reusable device, the adhesive layer 64 may therefore be disposable such that the front end 52 may be sterilized in any of a variety of known sterilization techniques, including cleaning with solvents or autoclaving. In the reusable embodiment, a new adhesive layer 64 is applied to the front end 52 prior to use on the patient. In a still further embodiment, the adhesive layer 64 is an adhesive applied to the front end 52.

The electronics 56 further include an ultrasound controller 66. The ultrasound controller 66 may exemplarily be a high performance 16 bit digital signal controller; however, it may be recognized that a variety of controllers may be deemed as suitable by a person of ordinary skill in the art to achieve the features and functionalities as disclosed herein. In one embodiment, the controller 66 is a dsPIC33 digital signal controller available from Microchip. In embodiments, the ultrasound controller 66 either includes read only memory (ROM) (not depicted) or is communicatively connected to ROM, exemplarily FLASH member (not depicted). Computer readable code is programmed to the ROM and the ultrasound controller 66 executes the computer readable code stored in the ROM, which causes the ultrasound controller 66 to execute the functionalities as disclosed herein.

The ultrasound controller 66 includes a timer or pulse wave modulator that produces alternating timing pulses. One of the timing pulses is a high frequency ultrasound control signal 70 that is provided to transmitter 68. The transmitter 68 amplifies the ultrasound control signal 70. The transmitter 68 converts the control signal 70 into a sinusoidal wave which is transmitted to the ultrasound crystal 58. In one embodiment, the high frequency ultrasound control signal 70 is at a frequency of about 1 MHz. It will be recognized by a person of ordinary skill in the art that alternative frequencies of ultrasound pulses may be used as the high frequency ultrasound control signal 70.

The ultrasound crystal 58 produces the transmitted ultrasound signal as described above in response to the sinusoidal wave from the transmitter 68. The ultrasound crystal 58 further receives the reflected ultrasound signals. As noted above, the reflected ultrasound signals exhibit a doppler shift due to the flow of blood in at least one of the major vessels of the fetus. The reflected ultrasound signals are processed by an amplifier 72. The second alternating timing pulse produced by the controller 66 is a receive window timing signal 78. The receive window timing signal 78 is sent to the amplifier 72 from the ultrasound controller 66. The amplifier 72 may be any of a variety of amplifiers, gain filters, or a combination thereof. Exemplary, the amplifier 72 is a band pass filter with a narrow pass band, exemplarily at 1 MHz. Alternatively, the amplifier 72 is a low-noise amplifier. The amplified reflected ultrasound signals 74 are processed by an analog-to-digital converter (ADC) 76 before the ultrasound signals 74 are provided to the controller 66. The ADC may exemplarily be a 16 bit analog to digital converter. In an exemplary embodiment, the ADC operates at a sampling frequency of at least two million samples per second. However, it will be recognized by one of ordinary skill in the art that alternative specifications of an ADC 76 may be used in connection with embodiments of the systems and devices as disclosed herein. In one embodiment, the ADC 76 is an integral part of the controller 66. In an alternative embodiment, the ADC 76 is a separate component communicatively connected to the controller 66.

The ultrasound controller 66 receives the digitized received reflected ultrasound signal and in an embodiment processes the ultrasound signal. The digitized ultrasound signal is demodulated by multiplying the digitized ultrasound signal by the ultrasound control signal 70 that had been previously provided to the transmitter 68. The controller 66 samples and holds the demodulated signal by storing the resulting low-frequency value in memory of the controller 66. The resulting low-frequency value is amplified using an automated gain control algorithm with an exemplary range of 0-40 DP of gain.

The ultrasound controller 66 down converts the digitized received reflected ultrasound signal to a low frequency ultrasound audio signal which is output by a digital-to-analog converter (DAC) 80. The low frequency ultrasound audio signal may exemplarily be 3.1 KHz. It is understood that the low frequency ultrasound audio signal may include frequencies above or below this frequency. In one embodiment, the DAC 80 is an integral part of the controller 66. In an alternative embodiment, the DAC 80 is a separate component communicatively connected to the controller 66. The DAC 80 of the ultrasound controller 66 transmits the ultrasound audio signal to a wireless transmitter 84.

In an embodiment, the wireless transmitter 84 is a Bluetooth head set and the Bluetooth head set receives the ultrasound audio signal 82 with a microphone input 86. The Bluetooth head set includes a Bluetooth head set (BTHS) module. The BTHS module includes headset software profile (HSP) that is well suited for the transmission and receipt of demodulated ultrasound signals. The BTHS module and the HSP in an embodiment are selected for maximum audio bandwidth. Exemplarily, the BTHS module is a Class 2 module such as an ARF 32 module available from Adeunis or a BTM511 module available from Laird. However, it will be recognized that a variety of BTHS modules, including Class 1 modules, may also be used with embodiments described herein. The DAC 80 matches the resolution of the BTHS module. Typically, this is 16 bits for stereo broadcast and 13 bits for mono broadcast. A still further embodiment connects the universal asynchronous receiver transmitter of the controller 66 to the Bluetooth head set 84 rather than through the DAC 80.

The wireless transmitter 84 and the ultrasound controller 66 receive electrical energization from a battery 88. In an embodiment, the battery 88 is a disposable watch or coin style battery. However, it may be recognized that alternative embodiments include other styles of batteries, including rechargeable batteries.

The wireless transmitter 84 produces a wireless signal 90 of the ultrasound audio signal. While the exemplary embodiments described herein have referred to radio frequency (RF) technology, in alternative embodiments, other forms of wireless communication may be conceivably be used including infrared or other optical communications and the current disclosure is not considered to be limited to RF communication.

Referring specifically to FIG. 3, a back end 98 of the fetal scalp doppler 50 is located remote to the front end 52. The back end 98 receives the wireless signal 90 with a wireless receiver 92. The back end 98 includes a patient monitoring device 94 that operates, such as with a processor (not depicted) connected to a computer readable medium (not depicted) upon which a computer readable code is stored such that the patient monitoring device 94 operates to process the received ultrasound audio signal and to derive the fetal pulse rate from the received ultrasound signal. As noted above, the doppler signal of the blood flow in the carotid artery and the jugular vein of the fetus produce repeating signals with a positive doppler shift for the carotid artery and a negative doppler shift for the jugular vein. The patient monitoring device 94 analyzes the timing of these repeating features to determine a fetal pulse rate. The patient monitoring device 94 (through the processor) extracts the fetal pulse rate from the received ultrasound audio signal. In one embodiment, this is accomplished by first applying an envelope detection technique, then the processor applies an autocorrelation technique to the detected envelope to extract the fetal pulse rate from the received ultrasound audio signal.

The patient monitoring device 94, and in particular the processor (not depicted) of the patient monitoring device 94 operates the display 96 to present the derived fetal pulse rate to a clinician. As noted above, particularly when taken with respect to a major vessel of the circulatory system, pulse rate is an effective analog for heart rate. In an embodiment, the fetal pulse rate may be presented as the FHR for clarity of clinician understanding and the pulse rate's approximation of heart rate.

In one embodiment, the back end 98 is a tablet PC. The processor of the tablet PC acts as the patient monitoring device 94 and a built in Bluetooth receiver is the wireless receiver 92. Non-limiting examples of such a tablet PC include the HT-1060 available from Heighton UMPC or MICA-101 available from Advantech.

Figure 5:
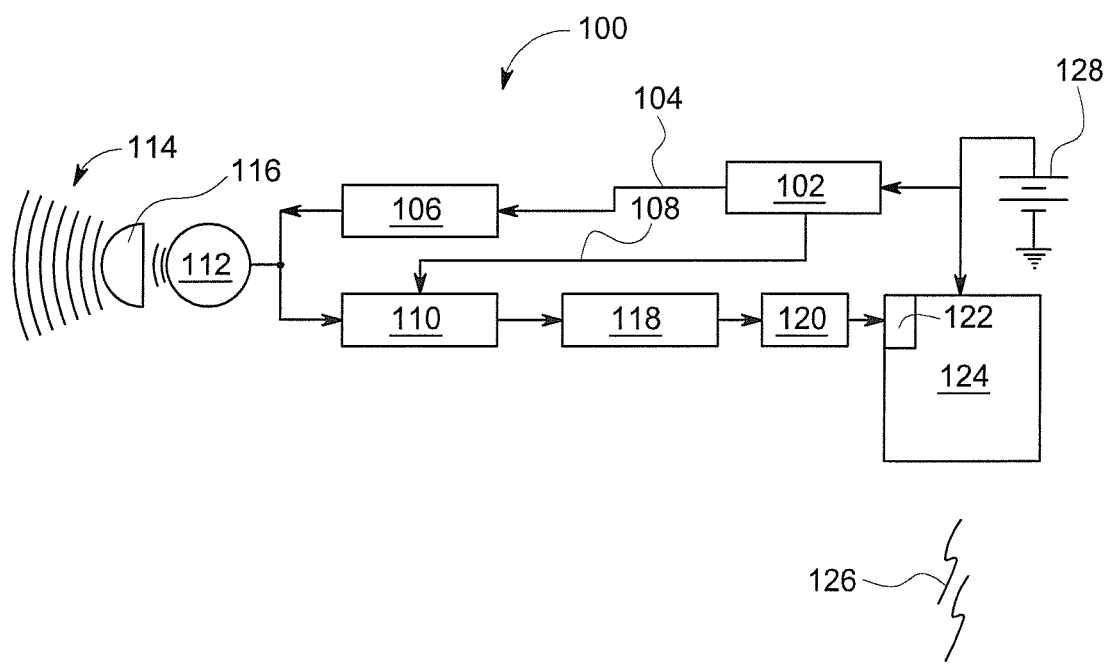
FIG. 5 is a schematic diagram of an alternative embodiment of the fetal scalp doppler front end.

FIG. 5 depicts an alternative analog implementation of the front end 100 of the fetal scalp doppler. It is understood that while FIGS. 4 and 5 depict alternative embodiments of the front end, a person of ordinary skill in the art will recognize alternative embodiments that use a compatible combination of the components of these two embodiments.

The front end 100 includes controller 102. The controller 102 may exemplarily be a microcontroller such as the DSPIC Microchip or MSP430 from Texas Instruments; however, a person of ordinary skill in the art will recognize alternative microcontrollers that may also be suitably used. The controller 102 includes a pulse width modulator that produces alternating timing pulses. The alternating timing pulses are a transmit pulse 104 that is provided to a transmitter 106 and a receive window 108 that is sent to an amplifier 110. In an exemplarily embodiment of the timing, the transmit pulse 104 and the receive window 108 are each 50 microseconds in duration in an alternating basis.

The transmitter 106 amplifies the transmit pulse 104 generated by the controller 102. In an embodiment, the transmit pulse 104 is a 1 MHz rectangular pulse. The transmitter converts the transmit pulse 104 into a sinusoidal wave which is transmitted to an ultrasound transducer 112 which produces an ultrasonic signal 114 as has been disclosed in further detail herein. The ultrasound transducer 112 is exemplarily a piezoelectric disk.

An acoustic lens 116 is placed in close proximity to the ultrasound transducer 112. The acoustic lens 116 shapes the ultrasound beam 114 produced by the ultrasound transducer 112. In an exemplary embodiment, the acoustic lens 116 diverges the ultrasound signal 114 such that the projected ultrasound beam encompasses a larger physical area of the fetus.

The ultrasound transducer 112 receives reflected returned ultrasound signals as has been disclosed above. These returned ultrasound signals are provided to the amplifier 110. The amplifier 110 is exemplarily a band pass filter (BPF) with a narrow pass band at 1 MHz. Additionally, the amplifier 110 is an 80 dB low-noise amplifier. It will be understood by one of ordinary skill in the art that various technical specifications of the amplifier 110 may be selected depending on an exact design or circumstances and still be within the scope of the present disclosure.

The filtered and amplified returned ultrasound signals are provided to a demodulator 118. The demodulator demodulates the signal by multiplying the input signal by the transmit pulse 104 that was provided to the transmitter 106. The demodulator 118 further samples and holds the demodulated signal by storing the resulting low-frequency value on a compacitor (not depicted). The resulting low-frequency value is provided to an automatic gain control (AGC) 120. The AGC is exemplarily in the range of 0-40 dB of gain. The amplified low-frequency value is provided to a microphone input 122 of wireless transmitter 124. Exemplarily, the wireless transmitter 124 is a Bluetooth head set wireless transmitter that includes a Bluetooth head set (BTHS) module that is selected for maximum audio bandwidth. Exemplarily, the BTHS module is a Class 2 module which may be exemplarily an ARF 32 module available from Adeunis or a BTM511 module available from Laird; however, it will be recognized by one of ordinary skill in the art that a variety of BTHS modules, including Class 1 modules, may also be used.

The maximum audio bandwidth is exemplarily 3.1 KHz for an ultrasound carrier frequency of 1 MHz. This is derived from the maximum velocity of blood in the carotid artery (approximately 2.3 meters per second) and the speed of sound transmission within the body (1540 meters per second).

The wireless transmitter 124 transmits the amplified low-frequency signal in a wireless transmission 126 which is received by a receiver of a back end (not depicted) as has been described herein.

A battery 128 supplies the electrical energization to both the controller 102 and the wireless transmitter 124.

Embodiments of the device and system as disclosed herein operate in a manner such that the fetal pulse monitor 52 is secured to the head of the fetus after the fetal membrane has been ruptured. Once secured to the fetus, the systems and devices disclosed herein provide fetal pulse monitoring during the last stage of labor and delivery. The pulse rate monitoring continues through this transition period and continuously into the first minutes and hours of the baby's life. Continual monitoring during the transition of birth provides the clinician with continuous access to diagnostic information of the newborn baby.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

What is claimed is:

1. A fetal pulse monitor configured to be secured to a head of a fetus comprising:
   an ultrasound crystal;
   an ultrasound controller electrically connected to the ultrasound crystal, the ultrasound controller operates the ultrasound crystal to produce ultrasound signals and receive reflected ultrasound signals which comprise a Doppler shift indicative of blood flow towards or away from the ultrasound crystal, the ultrasound controller receives the reflected ultrasound signals from the ultrasound crystal and down converts the reflected ultrasound signals to an audio signal;
   a wireless transmitter electrically connected to the ultrasound controller, the wireless transmitter receives the audio signal and transmits the audio signal modulated on a radio frequency signal to a patient monitoring device configured to derive a fetal pulse from the Doppler shift in the audio signal; and
   a biocompatible housing at least partially surrounding the ultrasound crystal, ultrasound controller, and the wireless transmitter, the biocompatible housing configured for insertion into a womb.

2. The fetal pulse monitor of claim 1, further comprising a battery within the biocompatible housing and electrically connected to the ultrasound controller and the wireless transmitter, wherein the battery supplies electrical energization to the ultrasound controller and the wireless transmitter.

3. The fetal pulse monitor of claim 1, wherein the wireless transmitter is a BLUETOOTH transmitter.

4. The fetal pulse monitor of claim 1, further comprising an acoustic lens disposed over the ultrasound crystal to shape the ultrasound beam produced by the ultrasound crystal.

5. The fetal pulse monitor of claim 4, wherein the Doppler shift in the received reflected ultrasound signals is indicative of blood flow in at least one of a carotid artery and a jugular vein of the fetus.

6. The fetal pulse monitor of claim 4, further comprising an adhesive layer disposed over the acoustic lens, the adhesive layer configured to adhere the fetal pulse monitor to the head of the fetus.

7. The fetal pulse monitor of claim 4, wherein the ultrasound crystal is a piezoelectric crystal.

8. The fetal pulse monitor of claim 7, wherein the ultrasound crystal is a plurality of ultrasound crystals.

9. The fetal pulse monitor of claim 1, wherein the ultrasound controller operates the ultrasound crystal at a high frequency, wherein the high frequency is about 1 Megahertz.

10. The fetal pulse monitor of claim 9, wherein the ultrasound controller converts the received high frequency ultrasound signal into the audio signal, wherein the audio signal is about 3.1 kilohertz.

11. A system for monitoring fetal pulse rate, the system comprising:

a fetal pulse monitor configured for insertion into a womb of a patient and for attachment to a fetus within the womb, the fetal pulse monitor including:
an ultrasound crystal;
an ultrasound controller electrically connected to the ultrasound crystal, the ultrasound controller operates the ultrasound crystal to produce ultrasound signals and receive reflected ultrasound signals, the ultrasound controller receives the reflected ultrasound signals from the ultrasound crystal and down converts the reflected ultrasound signals to an ultrasound audio signal;
a wireless transmitter electrically connected to the ultrasound controller, the wireless transmitter transmits the ultrasound audio signal modulated on a radio frequency signal; and
a biocompatible housing at least partially surrounding the ultrasound crystal, ultrasound controller, and the wireless transmitter, the biocompatible housing configured for insertion into a womb for monitoring a fetus within the womb;
a patient monitoring device external to the womb, the patient monitoring device includes:
a wireless receiver that receives the ultrasound audio signal from the wireless transmitter; and
a processor that detects the instantaneous fetal pulse rate from the received ultrasound audio signal from Doppler shifts in the ultrasound audio signal; and
a graphical display communicatively connected to the patient monitoring device, such that the graphical display is operated by the patient monitoring device to present the determined fetal pulse rate.

12. The system of claim 11, further comprising an acoustic lens disposed over the ultrasound crystal, the acoustic lens shapes the ultrasound signals produced by the ultrasound crystal.

13. The system of claim 12, wherein the fetal pulse monitor is at least partially disposed within a biocompatible housing.

14. The system of claim 13, wherein the fetal pulse monitor is configured to be removably secured to the head of the fetus.

15. A method of fetal pulse monitoring, the method comprising:
providing a fetal pulse monitoring device comprising an ultrasound crystal, an ultrasound controller electrically connected to the ultrasound crystal, a wireless transmitter connected to the ultrasound controller, and a biocompatible housing at least partially surrounding the ultrasound crystal, ultrasound controller, and the wireless transmitter, the biocompatible housing configured for insertion into a womb;
securing the fetal pulse monitoring device to the head of a fetus;
operating the ultrasound crystal with the ultrasound controller to produce ultrasound signals;
projecting the ultrasound signals at least through a portion of the head of the fetus;
receiving reflected ultrasound signals comprising a Doppler shift due to blood flow in at least one of the carotid artery and a jugular vein of the fetus at the ultrasound controller;
down converting the reflected ultrasound signals to produce an audio signal with the ultrasound controller;
transmitting, with the wireless transmitter, the audio signal modulated on a radio frequency signal to a patient monitoring device; and
deriving a fetal pulse with the patient monitoring device from the Doppler shift in the audio signal.

16. The method of claim 15, further comprising diverging the ultrasound signals form the ultrasound crystal with an acoustic lens.

17. The method of claim 15 wherein a frequency of the audio signal is less then or equal to 3.1 KHz.

18. The method of claim 15 further comprising:
deriving a fetal pulse from the audio signal antepartum; and
deriving a fetal pulse from the audio signal postpartum.

* * * * *